(12) United States Patent
Schubert et al.

(10) Patent No.: US 7,842,827 B2
(45) Date of Patent: Nov. 30, 2010

(54) MESOPOROUS METAL-ORGANIC FRAMEWORK

(75) Inventors: Markus Schubert, Ludwigshafen (DE); Ulrich Mueller, Neustadt (DE); Hendrick Mattenheimer, Ludwigshafen (DE); Markus Tonigold, Blaustein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 449 days.

(21) Appl. No.: 11/996,976

(22) PCT Filed: Aug. 16, 2006

(86) PCT No.: PCT/EP2006/065346

§ 371 (c)(1), (2), (4) Date: Jan. 28, 2008

(87) PCT Pub. No.: WO2007/023119

PCT Pub. Date: Mar. 1, 2007

(65) Prior Publication Data

US 2008/0188677 A1    Aug. 7, 2008

(30) Foreign Application Priority Data

Aug. 22, 2005   (DE) .................. 10 2005 039 654

(51) Int. Cl.
*C07F 5/06* (2006.01)
*B01J 33/00* (2006.01)

(52) U.S. Cl. .......................... 556/27; 502/2
(58) Field of Classification Search ............ 556/27; 502/2
See application file for complete search history.

(56) References Cited

U.S. PATENT DOCUMENTS 5,648,508 A   7/1997   Yaghi

FOREIGN PATENT DOCUMENTS

| DE | 101 11 230 | 9/2002 |
| EP | 0 790 253 | 8/1997 |
| JP | 59 155333 | 9/1984 |
| WO | 99 05151 | 2/1999 |
| WO | 02 070526 | 9/2002 |

OTHER PUBLICATIONS

U.S. Appl. No. 12/594,604, filed Oct. 5, 2009, Stein et al.
U.S. Appl. No. 12/597,616, filed Oct. 26, 2009, Schubert et al.
U.S. Appl. No. 12/601,022, filed Nov. 20, 2009, Schubert et al.
U.S. Appl. No. 12/600,539, filed Nov. 17, 2009, Schubert et al.
U.S. Appl. No. 12/668,436, filed Jan. 11, 2010, Schubert et al.
O'Keeffe, M., et al., "Frameworks for Extended Solids: Geometrical Design Principles", Journal of Solid State Chemistry, vol. 152, pp. 3 to 20, 2000.
Li, Hailian et al., "Design and Synthesis of an Exceptionally Stable and Highly Porous Metal-Organic Framework", Nature, vol. 42, pp. 276 to 279, 1999.
Eddaoudi, Mohamed et al., "Design and Synthesis of Metal-Carboxylate Frameworks With Permanent Microporosity", Topics in Catalysis 9, pp. 105 to 111, 1999.
Chen, Banglin et al., "Interwoven Metal-Organic Framework on a Periodic Minimal Surface With Extra-Large Pores", Science, vol. 291, pp. 1021 to 1023, 2001.
Loiseau, Thierry et al., "A Rationale for the Large Breathing of the Porous Aluminum Terephthalate (MIL-53) Upon Hydration", Chem. Eur. J., vol. 10, pp. 1373 to 1382, 2004.
Lin, Zheng-Zhong et al., Two Novel Inorganic-Organic Hybrid Frameworks Based on $IN^{III}$-BTC and $IN^{III}$-BTEC, Eur. J. Inorg. Chem., pp. 77 to 81, 2005.

*Primary Examiner*—Porfirio Nazario Gonzalez
(74) *Attorney, Agent, or Firm*—Oblon, Spivak, McClelland, Maier & Neustadt, L.L.P.

(57) ABSTRACT

The present invention relates to a porous metal-organic framework comprising $Al^{III}$ and at least one at least bidentate compound, wherein the at least one at least bidentate organic compound is a six-membered aromatic hydrocarbon ring A in which one or more ring carbons may be replaced by nitrogen and which has three substituents X and optionally one or more substituents selected from the group consisting of R, NRR', OR, SR, F, Cl and Br, where R, R' are each, independently of one another, hydrogen, methyl which may optionally be substituted by one or more fluorine atoms or ethyl which may optionally be substituted by one or more fluorine atoms and each X is, independently of the others, $C(=O)O^-$, $C(=S)O^-$, $C(=O)S^-$, $C(=S)S^-$ or a protonated form thereof. The invention further provides a process for preparing it and provides for the use of the new porous metal-organic framework.

14 Claims, 8 Drawing Sheets

MESOPOROUS METAL-ORGANIC FRAMEWORK

CROSS REFERENCE TO RELATED APPLICATION

This application is a 371 of PCT/EP06/065346, filed on Aug. 16, 2006, and claims priority to German Patent Application No. 10 2005 039 654.2, filed on Aug. 22, 2005.

The present invention relates to a porous metal-organic framework and a process for preparing it and its use.

Porous metal-organic frameworks are known in the prior art.

They typically comprise at least one at least bidentate organic compound coordinated to at least one metal ion. Such metal-organic frameworks (MOFs) are described, for example, in U.S. Pat. No. 5,648,508, EP-A 0 790 253, M. O. Keefe, J. Sol. State Chem. 152 (2000), 3-20; H. Li et al., Nature 402 (1999), 276; M. Eddaoudi, Topics in Catalysis 9 (1999), 105-111; B. Chen et al., Science 291 (2001), 1021-1023, and DE-A 101 11 230.

The metal-organic frameworks studied in the prior art have a variety of uses. They can be used, for example, for storage, separation or chemical reaction of substances. In particular, they can be used as supports for catalysts or catalysts.

In the search for further applications or to improve the properties of such metal-organic frameworks, numerous combinations of metal ions and at least bidentate organic compounds have been tested. Recently, metal-organic frameworks in which the metal ion is a main group element of the Periodic Table have also come under consideration.

T. Loiseau et al., Chem. Eur. J. 10 (2004), 1373-1382, describe, for example, porous aluminum terephthalate. However, this has pores of comparably small size. This is in a range as is also known and customary for other metal-organic frameworks based on other metals such as zinc. This is particularly disadvantageous for reactions in which comparatively large-volume reactants are reacted in a diffusion-limited reaction.

Z.-Z. Lin et al., Eur. J. Inorg. Chem. 2005, 77-81, describe a framework based on $In^{III}$—BTC (BTC=1,3,5-benzenetricarboxylic acid). However, the framework obtained in this way has poor absorption properties, if any. This is particularly disadvantageous for applications in the field of separation or storage of compounds, in particular gases.

There is therefore a continuing need for the provision of new metal-organic frameworks which have at least partly superior properties compared to the frameworks known in the prior art.

It is therefore an object of the present invention to provide a porous metal-organic framework which has the properties indicated above.

This object is achieved by a porous metal-organic framework comprising at least one at least bidentate organic compound coordinated to at least one metal ion, wherein the at least one metal ion is $Al^{III}$ and the at least one at least bidentate organic compound is a six-membered aromatic hydrocarbon ring A in which one or more ring carbons may be replaced by nitrogen and which has three substituents X and optionally one or more substituents selected from the group consisting of R, NRR', OR, SR, F, Cl and Br, where R, R' are each, independently of one another, hydrogen, methyl which may optionally be substituted by one or more fluorine atoms or ethyl which may optionally be substituted by one or more fluorine atoms and each X is, independently of the others, $C(=O)O^-$, $C(=S)O^-$, $C(=O)S^-$, $C(=S)S^-$ or a protonated form thereof.

It has been found that frameworks as described above have a comparatively high proportion of large-volume pores (mesopores) and likewise have comparatively high specific surface areas, which leads to advantages in the applications described below. This is particularly surprising since these properties are not retained when aluminum is replaced by its analogue indium in the same group of the Periodic Table or an organic compound substituted by only two groups X is used in place of the organic compound substituted by three groups X for building up a metal-organic framework. This is particularly true when the organic compound is a benzenetricarboxylate.

In addition, the X-ray diffraction patterns of the framework of the invention barely display the sharp signals in the range from 5 to 30°(2Θ), in particular from 5 to 12°, characteristic of the abovementioned frameworks known from the prior art.

The metal-organic framework comprises at least one at least bidentate organic compound which is a six-membered aromatic hydrocarbon ring A in which one or more ring carbons may be replaced by nitrogen and which has three substituents X and optionally one or more substituents selected from the group consisting of R, NRR', OR, SR, F, Cl and Br, where R, R' are each, independently of one another, hydrogen, methyl which may optionally be substituted by one or more fluorine atoms or ethyl which may optionally be substituted by one or more fluorine atoms and each X is, independently of the others, $C(=O)O^-$, $C(=S)O^-$, $C(=O)S^-$, $C(=S)S^-$ or a protonated form thereof. Further organic compounds, in particular one or more monodentate ligands, may also occur in the framework. However, preference is given to the mole fraction of the first-mentioned organic compound which has to be present in at least 50%, more preferably at least 75% and particularly preferably at least 90%, of the total amount of the organic compounds in the framework.

The ring A is preferably a benzene, pyridine, pyridazine, pyrimidine, pyrazine or triazine ring. A is particularly preferably benzene.

Furthermore, the ring A has three substituents X. These are carboxylate groups and/or their thio analogues. At least part of the carboxylate groups and/or thio analogues occurring on A in the framework can be present in protonated form.

In addition, the ring A can have one or more further substituents. These are the functional groups R, NRR', OR, SR, F, Cl and Br, where R and R' can each be, independently of one another, hydrogen, methyl or ethyl. The methyl and ethyl groups can also be monofluorinated or polyfluorinated. However, the ring A preferably has no further substituents apart from X.

The organic compound is particularly preferably 1,2,3-, 1,2,4- or 1,3,5-benzene-tricarboxylate or an at least partially protonated analogue thereof. Very particular preference is given to 1,3,5-benzenetricarboxylate.

The metal-organic framework of the invention comprises pores, in particular micropores and/or mesopores. Micropores are defined as pores having a diameter of 2 nm or less and mesopores are defined by a diameter in the range from 2 to 50 nm, in each case in accordance with the definition given in Pure Applied Chemistry 57 (1985), pages 603-619, in particular on page 606. The presence of micropores and/or mesopores can be checked by means of sorption measurements, with these measurements determining the uptake capacity for nitrogen of the metal-organic frameworks at 77 K in accordance with DIN 66131 and/or DIN 66134.

The metal-organic framework of the invention preferably has an average pore diameter of from 2 to 10 nm, particularly preferably from 3 to 9 nm. Particular preference is given to the dispersion of the pore sizes being not more than +/−5 nm. Furthermore, the most frequently occurring pore diameter is preferably in a range from 3 to 9 nm.

The specific surface area, calculated according to the Langmuir model in accordance with DIN 66135 (DIN 66131, 66134), of a metal-organic framework according to the invention in powder form is preferably at least 800 $m^2/g$. The specific surface area is more preferably at least 1000 $m^2/g$ and particularly preferably at least 1300 $m^2/g$. The specific surface area is very particularly preferably at least 1500 $m^2/g$.

Preference is given to at least 50% of the pore volume being formed by pores having a pore diameter of from 2 to 10 nm (mesopores). The proportion of the pore volume is preferably at least 65%, very particularly preferably at least 80%. The pore volume is preferably at least 0.8 ml/g, more preferably at least 1.1 ml/g.

Shaped MOF bodies can have a low specific surface area. However, this is preferably more than 10 $m^2/g$, more preferably more than 50 $m^2/g$ and even more preferably more than 500 $m^2/g$.

Apart from the above-described pores, a shaped body comprising the metal-organic framework of the invention also has larger pores whose size distribution can vary. However, preference is given to more than 50% of the total pore volume, in particular more than 75%, being made up by pores having a pore diameter of up to 1000 nm. However, a large part of the pore volume is preferably formed by pores from two diameter ranges. Further preference is therefore given to more than 25% of the total pore volume, in particular more than 50% of the total pore volume, being formed by pores which are in a diameter range of from 100 nm to 800 nm and more than 15% of the total pore volume, in particular more than 25% of the total pore volume, being formed by pores in a diameter range up to 10 nm. The pore distribution can be determined by means of mercury porosimetry.

The present invention further provides a process for preparing a framework according to the invention, which comprises the step reaction of at least one metal compound with at least one at least bidentate organic compound which can coordinate to the metal ion, wherein the metal is $Al^{III}$ and the at least one at least bidentate organic compound is a six-membered aromatic hydrocarbon ring A in which one or more ring carbons may be replaced by nitrogen and which has three substituents X and optionally one or more substituents selected from the group consisting of R, NRR', OR, SR, F, Cl and Br, where R, R' are each, independently of one another, hydrogen, methyl which may optionally be substituted by one or more fluorine atoms or ethyl which may optionally be substituted by one or more fluorine atoms and each X is, independently of the others, $C(=O)O^-$, $C(=S)O^-$, $C(=O)S^-$, $C(=S)S^-$ or a protonated form thereof.

The reaction preferably takes place in a nonaqueous organic solvent while stirring at a pressure of not more than 2 bar (absolute).

The pressure is more preferably not more than 1230 mbar (absolute). Even more preferably, the reaction takes place under atmospheric pressure.

The metal-organic framework of the invention can also be prepared in water as solvent with addition of a base.

However, the use of a nonaqueous organic solvent makes it possible to dispense with the base. It is, however, likewise possible to add a base. The organic solvent itself can also serve as base.

Preferred starting materials when using an aluminum salt in the synthesis are the hydrates of aluminum chloride or nitrate, particularly preferably the chloride.

Furthermore, the metal compound used for preparing the porous metal-organic framework of the invention can preferably be nonionic and/or the counterion to the $Al^{III}$ cation can be derived from a protic solvent. The use of an appropriately chosen nonionic compound makes it possible to avoid the presence of the metal in the form of a salt in the reaction to form the porous metal-organic framework and may thus make it possible to avoid any difficulties in the removal of the corresponding anion of the metal salt, as long as no further interfering salts are produced from the metal compound in the reaction. If the counterion is a solvent anion, this can, when chosen appropriately, be present after the reaction as solvent, which may be identical to or different from the nonaqueous organic solvent used. In the latter case, preference is given to this solvent being at least partially miscible with the nonaqueous organic solvent.

Nonionic compounds or counterions to the metal cation which can be derived from protic solvents can be, for example, metal alkoxides, for example methoxides, ethoxides, propoxides, butoxides. Oxides or hydroxides are likewise conceivable.

The nonaqueous organic solvent is preferably a $C_{1-6}$-alkanol, dimethyl sulfoxide (DMSO), N,N-dimethylformamide (DMF), N,N-diethylformamide (DEF), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), γ-butyrolactone, alicyclic alcohols such as cyclohexanol, ketones such as acetone or acetylacetone, cyclic ketones such as cyclohexanone, sulfolene or a mixture thereof.

A $C_{1-6}$-alkanol is an alkanol having from 1 to 6 carbon atoms. Examples are methanol, ethanol, n-propanol, i-propanol, n-butanol, i-butanol, t-butanol, pentanol, hexanol and mixtures thereof.

An optionally halogenated $C_{1-200}$-alkane is an alkane which has from 1 to 200 carbon atoms and in which one or more to all hydrogen atoms may be replaced by halogen, preferably chlorine or fluorine, in particular chlorine. Examples are chloroform, dichloromethane, tetrachloromethane, dichloroethane, hexane, heptane, octane and mixtures thereof.

Preferred solvents are DMF, DEF and NMP. Particular preference is given to DMF.

The term "nonaqueous" preferably refers to a solvent which has a maximum water content of 10% by weight, more preferably 5% by weight, even more preferably 1% by weight, still more preferably 0.1% by weight, particularly preferably 0.01% by weight, based on the total weight of the solvent.

The maximum water content during the reaction is preferably 10% by weight, more preferably 5% by weight and even more preferably 1% by weight.

The term "solvent" encompasses both pure solvents and mixtures of different solvents.

Furthermore, the process step of reaction of the at least one metal compound with the at least one at least bidentate organic compound is preferably followed by a calcination step. The temperature set here is typically above 250° C., preferably from 300 to 400° C.

The calcination step can remove the ligand present in the pores.

In addition or as an alternative thereto, the removal of ligand from the pores of the porous metal-organic framework can be effected by treatment of the framework formed with a nonaqueous solvent. Here, the ligand is removed in the manner of an "extraction process" and, if appropriate, replaced in the framework by a solvent molecule. The extraction process preferably takes place before a calcination, if the latter is provided.

The treatment is preferably carried out for at least 30 minutes and can typically be carried out for up to two days. This can occur at room temperature or at elevated temperature. It is preferably carried out at elevated temperature, for example at least 40° C., preferably 60° C. Further preference is given to a reaction at the boiling point of the solvent (reflux).

The treatment can be carried out in a simple vessel by slurrying and stirring the framework. It is also possible to use extraction apparatuses such as Soxlet apparatuses, in particular industrial extraction apparatuses.

Suitable solvents are those mentioned above, i.e. $C_{1-6}$-alkanol, DMSO, DMF, DEF, acetonitrile, toluene, dioxane, benzene, chlorobenzene, MEK, pyridine, THF, ethyl acetate, optionally halogenated $C_{1-200}$-alkane, sulfolene, glycol, NMP or mixtures thereof.

The solvent used for extraction can be identical to or different from that used for the reaction of the at least one metal compound with the at least one at least bidentate organic compound. In particular, it is not absolutely necessary that the solvent used in the extraction is water-free.

A preferred extractant is methanol, ethanol, acetone, MEK or a mixture thereof. Particular preference is given to methanol.

The present invention further provides a process for preparing the metal-organic framework of the invention, in which $Al^{III}$ is made available for the reaction by means of anodic oxidation.

The preparation of metal-organic frameworks by an electrochemical route is described in WO-A 2005/049892.

The metal-organic framework of the invention can be present in powder form or as agglomerate. The framework can be used as such or it is converted into a shaped body. Preferred processes here are extrusion or tableting. In the production of shaped bodies, the framework can comprise further materials such as binders, lubricants or other additives which are added during production. It is likewise conceivable for the framework to comprise further constituents, for example adsorbents such as activated carbon or the like.

The possible geometries of these shaped bodies are subject to essentially no restrictions. Examples are, inter alia, pellets such as disk-shaped pellets, pills, spheres, granules, extrudates such as rod extrudates, honeycombs, grids and hollow bodies.

All suitable processes are in principle possible for producing these shaped bodies. In particular, the following processes are preferred:

kneading/pan milling of the framework either alone or together with at least one binder and/or at least one pasting agent and/or at least one template compound to give a mixture; shaping of the resulting mixture by means of at least one suitable method, for example extrusion; optionally washing and/or drying and/or calcination of the extrudate; optionally finishing.

Application of the framework to at least one optionally porous support material. The material obtained can then be processed further by the method described above to give a shaped body.

Application of the framework to at least one optionally porous substrate.

Kneading/pan milling and shaping can be carried out by any suitable method, as described, for example, in Ullmanns Enzyklopädie der Technischen Chemie, 4th edition, Volume 2, p. 313 ff. (1972).

For example, the kneading/pan milling and/or shaping can preferably be carried out by means of a piston press, roll press in the present or absence of at least one binder material, compounding, pelletization, tableting, extrusion, coextrusion, foaming, spinning, coating, granulation, preferably spray granulation, spraying, spray drying or a combination of two or more of these methods.

Very particular preference is given to producing pellets and/or tablets.

The kneading and/or shaping can be carried out at elevated temperatures, for example in the range from room temperature to 300° C., and/or at elevated pressure, for example in the range from atmospheric pressure to a few hundred bar, and/or in a protective gas atmosphere, for example in the presence of at least one noble gas, nitrogen or a mixture of two or more thereof.

The kneading and/or shaping is, according to a further embodiment, carried out with addition of at least one binder, with the binder used being able in principle to be any chemical compound which ensures the desired viscosity for kneading and/or shaping the composition. Accordingly, binders can, for the purposes of the present invention, be either viscosity-increasing or viscosity-reducing compounds.

Preferred binders include, for example, aluminum oxide or binders comprising aluminum oxide as described, for example, in WO 94/29408, silicon dioxide as described, for example, in EP 0 592 050 A1, mixtures of silicon dioxide and aluminum oxide as described, for example, in WO 94/13584, clay minerals as described, for example, in JP 03-037156 A, for example montmorillonite, kaolin, bentonite, hallosite, dickite, nacrite and anauxite, alkoxysilanes as described, for example, in EP 0 102 544 B1, for example tetraalkoxysilanes such as tetramethoxysilane, tetraethoxysilane, tetrapropoxysilane, tetrabutoxysilane, and, for example, trialkoxysilanes such as trimethoxysilane, triethoxysilane, tripropoxysilane, tributoxysilane, alkoxytitanates, for example tetraalkoxytitanates such as tetramethoxytitanate, tetraethoxytitanate, tetrapropoxytitanate, tetrabutoxytitanate, and, for example, trialkoxytitanates such as trimethoxytitanate, triethoxytitanate, tripropoxytitanate, tributoxytitanate, alkoxyzirconates, for example tetraalkoxyzirconates such as tetramethoxyzirconate, tetraethoxyzirconate, tetrapropoxyzirconate, tetrabutoxyzirconate, and, for example, trialkoxyzirconates such as trimethoxyzirconate, triethoxyzirconate, tripropoxyzirconate, tributoxyzirconate, silica sols, amphiphilic substances and/or graphites. Particular preference is given to graphite.

As viscosity-increasing compound, it is also possible, for example, to use, if appropriate in addition to the abovementioned compounds, an organic compound and/or a hydrophilic polymer such as cellulose or a cellulose derivative such as methylcellulose and/or a polyacrylate and/or a polymethacrylate and/or a polyvinyl alcohol and/or a polyvinylpyrrolidone and/or a polyisobutene and/or a polytetrahydrofuran and/or a polyethylene oxide.

As pasting agent, preference is given to using, inter alia, water or at least one alcohol, for example a monoalcohol having from 1 to 4 carbon atoms, e.g. methanol, ethanol, n-propanol, isopropanol, 1-butanol, 2-butanol, 2-methyl-1-propanol or 2-methyl-2-propanol, or a mixture of water and at least one of the alcohols mentioned or a monohydric alcohol such as a glycol, preferably a water-miscible polyhydric alcohol, either alone or as a mixture with water and/or at least one of the monohydric alcohols mentioned.

Further additives which can be used for kneading and/or shaping are, inter alia, amines or amine derivatives such as tetraalkylammonium compounds or amino alcohols and carbonate-comprising compounds such as calcium carbonate. Such further additives are described, for instance, in EP 0 389 041 A1, EP 0 200 260 A1 or WO95/19222.

The order of addition of the additives such as template compound, binder, pasting agent, viscosity-increasing substance in shaping and kneading is in principle not critical.

In a further preferred embodiment of the process of the invention, the shaped body obtained by kneading and/or shaping is subjected to at least one drying operation which is generally carried out a temperature in the range from 25 to 300° C., preferably in the range from 50 to 300° C. and particularly preferably in the range from 100 to 300° C. It is likewise possible to carry out drying under reduced pressure or under a protective gas atmosphere or by spray drying.

In a particularly preferred embodiment, at least one of the compounds added as additives is at least partly removed from the shaped body during this drying operation.

The present invention further provides for the use of the porous metal-organic framework of the invention for the uptake of at least one substance for the purposes of its storage, separation, controlled release or chemical reaction and also as support material, for example for metals, metal oxides, metal sulfides or other framework structures, and in catalysis.

The at least one substance can be a gas or a liquid. The substance is preferably a gas.

For the purposes of the present invention, the terms "gas" and "liquid" are used in the interests of simplicity, but gas mixtures and liquid mixtures or liquid solutions are likewise encompassed by the term "gas" or "liquid".

Preferred gases are hydrogen, hydrocarbons, in particular methane, ethane, ethene, acetylene, propane, n-butane and i-butane, carbon monoxide, carbon dioxide, nitrogen oxides, oxygen, sulfur oxides, halogens, halogenated hydrocarbons, $NF_3$, $SF_6$, ammonia, boranes, phosphanes, hydrogen sulfide, amines, formaldehyde, noble gases, in particular helium, neon, argon, krypton and xenon.

Particular preference is given to the use of a metal-organic framework according to the invention for the storage of hydrogen and for diffusion-limited reaction with large-volume reactants. Preference is also given to the storage of comparatively large substances which typically cannot be stored, or be stored only unsatisfactorily, in other metal-organic frameworks or other porous materials such as zeolites. Examples are dyes (pigments) or small proteins, e.g. enzymes.

The abovementioned reactions can be hydrogenations, oxidations in the liquid phase, metathesis in the liquid phase, alkoxylations, etherifications, esterifications, alkylations, hydrolyses or comparable reactions. Typical large reactants in diffusion-limited reactions can be, for example, polyols, substituted benzenes, dyes or other compounds.

The at least one substance can, as described above, also be a liquid. Examples of such a liquid are disinfectants, inorganic or organic solvents, fuels, in particular gasoline or diesel, hydraulic fluid, radiator fluid, brake fluid or an oil, in particular machine oil. The liquid can also be halogenated aliphatic or aromatic, cyclic or acyclic hydrocarbons or a mixture thereof. In particular, the liquid can be acetone, acetonitrile, aniline, anisole, benzene, benzonitrile, bromobenzene, butanol, tert-butanol, quinoline, chlorobenzene, chloroform, cyclohexane, diethylene glycol, diethyl ether, dimethyl acetamide, dimethylformamide, dimethyl sulfoxide, dioxane, glacial acetic acid, acetic anhydride, ethyl acetate, ethanol, ethylene carbonate, ethylene dichloride, ethylene glycol, ethylene glycol dimethyl ether, formamide, hexane, isopropanol, methanol, methoxypropanol, 3-methyl-1-butanol, methylene chloride, methyl ethyl ketone, N-methylformamide, N-methylpyrrolidone, nitrobenzene, nitromethane, piperidine, propanol, propylene carbonate, pyridine, carbon disulfide, sulfolane, tetrachloroethene, carbon tetrachloride, tetrahydrofuran, toluene, 1,1,1-trichloroethane, trichloroethylene, triethylamine, triethylene glycol, triglyme, water or a mixture thereof.

Furthermore, the at least one substance can be an odorous substance.

The odorous substance is preferably a volatile organic or inorganic compound which comprises at least one of the elements nitrogen, phosphorus, oxygen, sulfur, fluorine, chlorine, bromine or iodine or is an unsaturated or aromatic hydrocarbon or a saturated or unsaturated aldehyde or a ketone. More preferred elements are nitrogen, oxygen, phosphorus, sulfur, chlorine, bromine; and particular preference is given to nitrogen, oxygen, phosphorus and sulfur.

In particular, the odorous substance is ammonia, hydrogen sulfide, sulfur oxides, nitrogen oxides, ozone, cyclic or acylic amines, thiols, thioethers and aldehydes, ketones, esters, ethers, acids or alcohols. Particular preference is given to ammonia, hydrogen sulfide, organic acids (preferably acetic acid, propionic acid, butyric acid, isobutyric acid, valeric acid, isovaleric acid, caproic acid, heptanoic acid, lauric acid, pelargonic acid) and also cyclic or acyclic hydrocarbons which comprise nitrogen or sulfur and saturated or unsaturated aldehydes such as hexanal, heptanal, octanal, nonanal, decanal, octenal or nonenal and in particular volatile aldehydes such as butyraldehyde, propionaldehyde, acetaldehyde and formaldehyde and also fuels such as gasoline, diesel (constituents).

The odorous substances can also be fragrances which are used, for example, for producing perfumes. Examples of fragrances or oils which can release such fragrances are: essential oils, basil oil, geranium oil, mint oil, cananga oil, cardamom oil, lavender oil, peppermint oil, nutmeg oil, camomile oil, eucalyptus oil, rosemary oil, lemon oil, lime oil, orange oil, bergamot oil, muscatel sage oil, coriander oil, cypress oil, 1,1-dimethoxy-2-phenylethane, 2,4-dimethyl-4-phenyltetrahydrofuran, dimethyltetrahydrobenzaldehyde, 2,6-dimethyl-7-octen-2-ol, 1,2-diethoxy-3,7-dimethyl-2,6-octadiene, phenylacetaldehyde, rose oxide, ethyl 2-methylpentanoate, 1-(2,6,6-trimethyl-1,3-cyclohexadien-1-yl)-2-buten-1-one, ethyl vanillin, 2,6-dimethyl-2-octenol, 3,7-dimethyl-2-octenol, tert-butylcyclohexyl acetate, anisyl acetate, allyl cyclohexyloxyacetate, ethyllinalool, eugenol, coumarin, ethyl acetoacetate, 4-phenyl-2,4,6-trimethyl-1,3-dioxane, 4-methylene-3,5,6,6-tetramethyl-2-heptanone, ethyl tetrahydrosafranate, geranyl nitrile, cis-3-hexen-1-ol, cis-3-hexenyl acetate, cis-3-hexenyl methyl carbonate, 2,6-dimethyl-5-hepten-1-al, 4-(tricyclo[5.2.1.0]decylidene)-8-butanal, 5-(2,2,3-tri-methyl-3-cyclopentenyl)-3-methylpentan-2-ol, p-tert-butyl-alpha-methylhydro-cinnamaldehyde, ethyl[5.2.1.0]tricyclodecanecarboxylate, geraniol, citronellol, citral, linalool, linalyl acetate, ionone, phenylethanol and mixtures thereof.

For the purposes of the present invention, a volatile odorous substance preferably has a boiling point or boiling point range below 300° C. The odorous substance is more preferably a readily volatile compound or a mixture. The odorous substance particularly preferably has a boiling point or boiling range below 250° C., more preferably below 230° C., particularly preferably below 200° C.

Preference is likewise given to odorous substances which have a high volatility. The vapor pressure can be employed as a measure of the volatility. For the purposes of the present invention, a volatile odorous substance preferably has a vapor pressure of more than 0.001 kPa (20° C.). The odorous substance is more preferably a readily volatile compound or a mixture. The odorous substance particularly preferably has a vapor pressure of more than 0.01 kPa (20° C.), more preferably a vapor pressure of more than 0.05 kPa (20° C.). Particular preference is given to the odorous substances having a vapor pressure of more than 0.1 kPa (20° C.).

EXAMPLES

Example 1

Figure 1:
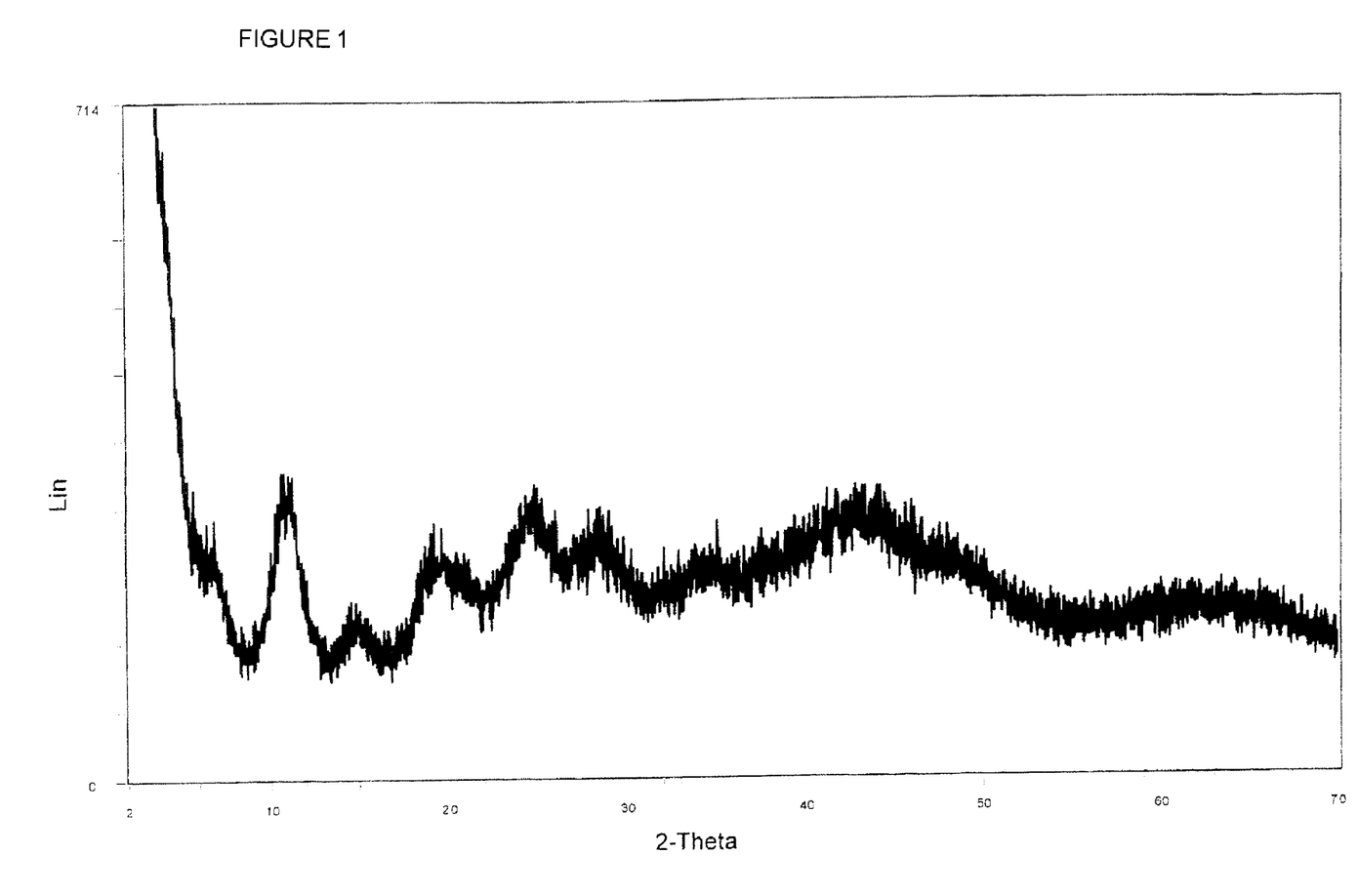
FIG. 1 shows the X-ray diffraction pattern (XRD) of the compound of Example 1.
Figure 8:
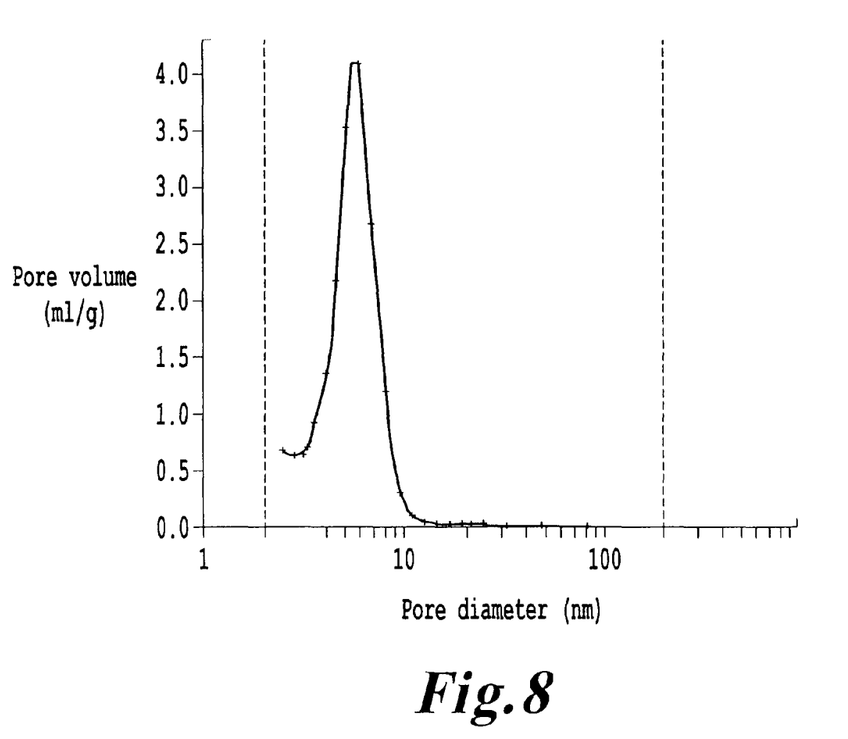
FIG. 8 shows the pore distribution for the compound of Example 1.

Atmospheric-Pressure Preparation/Characterization of an Al—BTC MOF 7.8 g of 1,3,5-benzenetricarboxylic acid and 22.9 g of $Al(NO_3)_3*9H_2O$ are suspended in 520.5 g of DMF in a glass flask and stirred under reflux at 130° C. for 4 days. After cooling, the solid is filtered off, washed with 2×100 ml of DMF and 4×100 ml of methanol and dried at 200° C. in a vacuum drying oven for 16 hours. The sample is subsequently after-treated at 330° C. in a muffle furnace (100 l/h of air) for 3 days (heating at about 75° C./h). 8.4 g of an Al—BTC MOF having a surface area of 1791 $m^2/g$ (determined using $N_2$ by the Langmuir method) are obtained. The X-ray diffraction pattern (XRD) is shown in FIG. 1. For all diffraction patterns, the sample is prepared unground under an $N_2$ bell jar and coated with a Styroflex film to make it airtight. The diffraction pattern of the sample is recorded on a D5000 instrument from Siemens using a Cu anode at a step width of 0.02° and a step rate of 3.6 s. The diffraction pattern shows, untypically for MOFs, barely any reflections and has a very amorphous appearance. The pore distribution is shown in FIG. 8. In FIG. 8 the pore volume V (ml/g) is depicted as a function of the pore diameter d (nm). Here, the unusually high (for MOFs) proportion of mesopores is apparent.

Example 2

Figure 2:
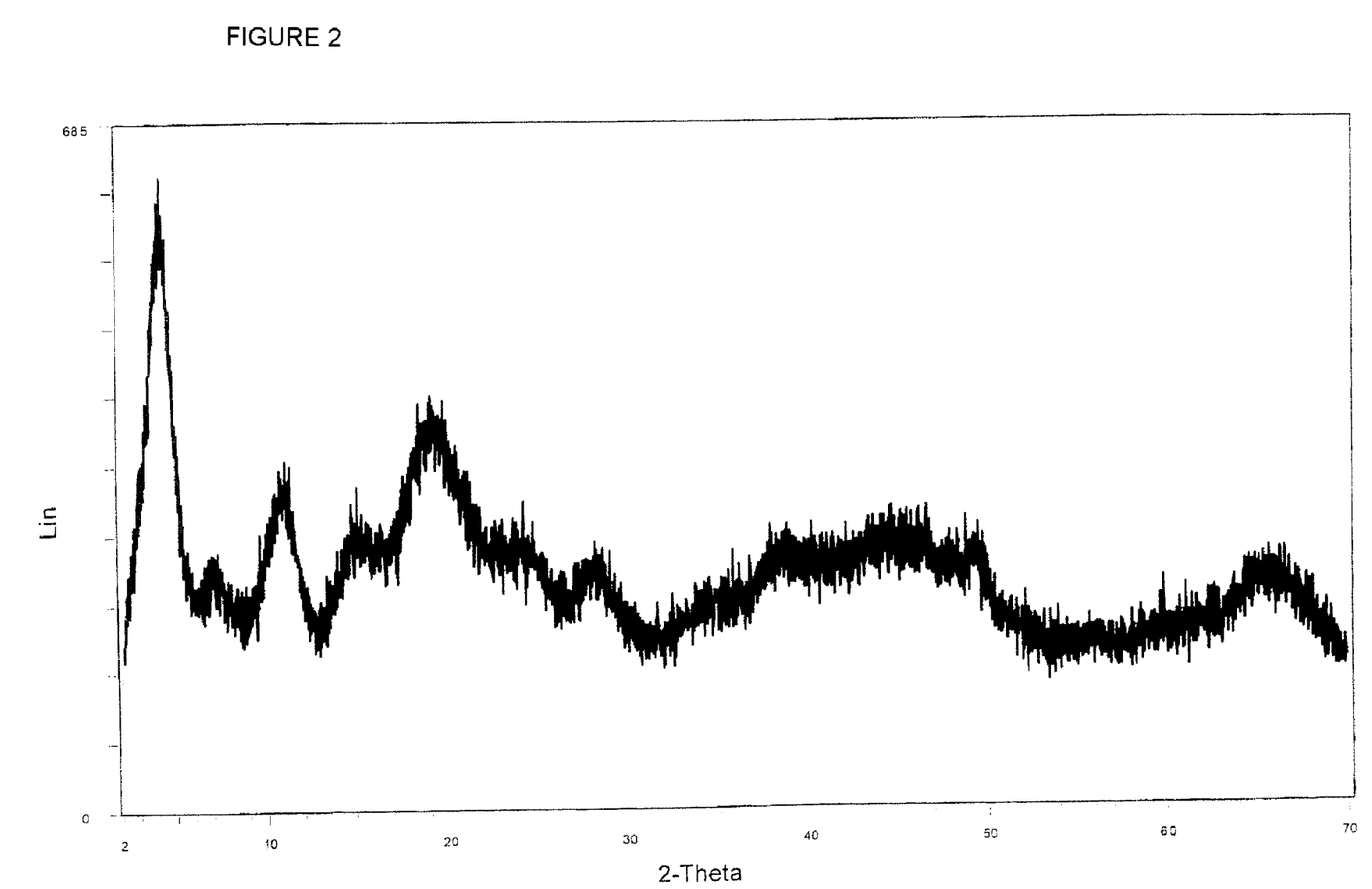
FIG. 2 shows the X-ray diffraction pattern (XRD) of the compound of Example 2.

Hydrothermal Preparation/Characterization of an Al—BTC MOF 2.46 g of 1,3,5-benzenetricarboxylic acid and 8.7 g of $Al(NO_3)_3*9H_2O$ are suspended in 33 ml of DMF. The mixture is heated at 170° C. in a Berghoff autoclave (Teflon liner) for 1 day. After cooling, the solid is filtered off, washed with DMF and methanol and dried at 200° C. in a vacuum drying oven for 5 hours. The sample is subsequently after-treated at 330° C. in a muffle furnace (100 l/h of air) for 3 days (heating at about 75° C./h). 2.5 g of an Al—BTC MOF having a surface area of 1516 $m^2/g$ (determined using $N_2$ by the Langmuir method) are obtained. The XRD is shown in FIG. 2. The diffraction pattern shows, untypically for MOFs, barely any reflections and has a very amorphous appearance.

Figure 3:
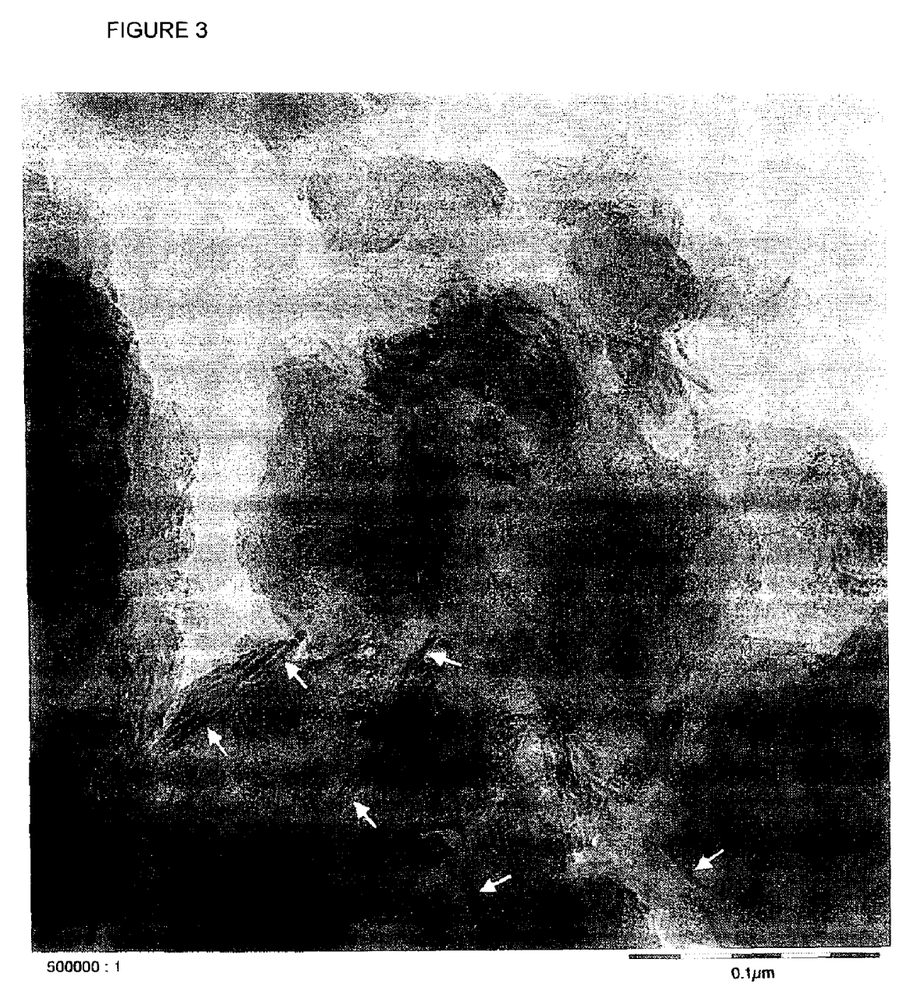
FIG. 3 shows a transmission electron micrograph of the compound of Example 2.
Figure 4:
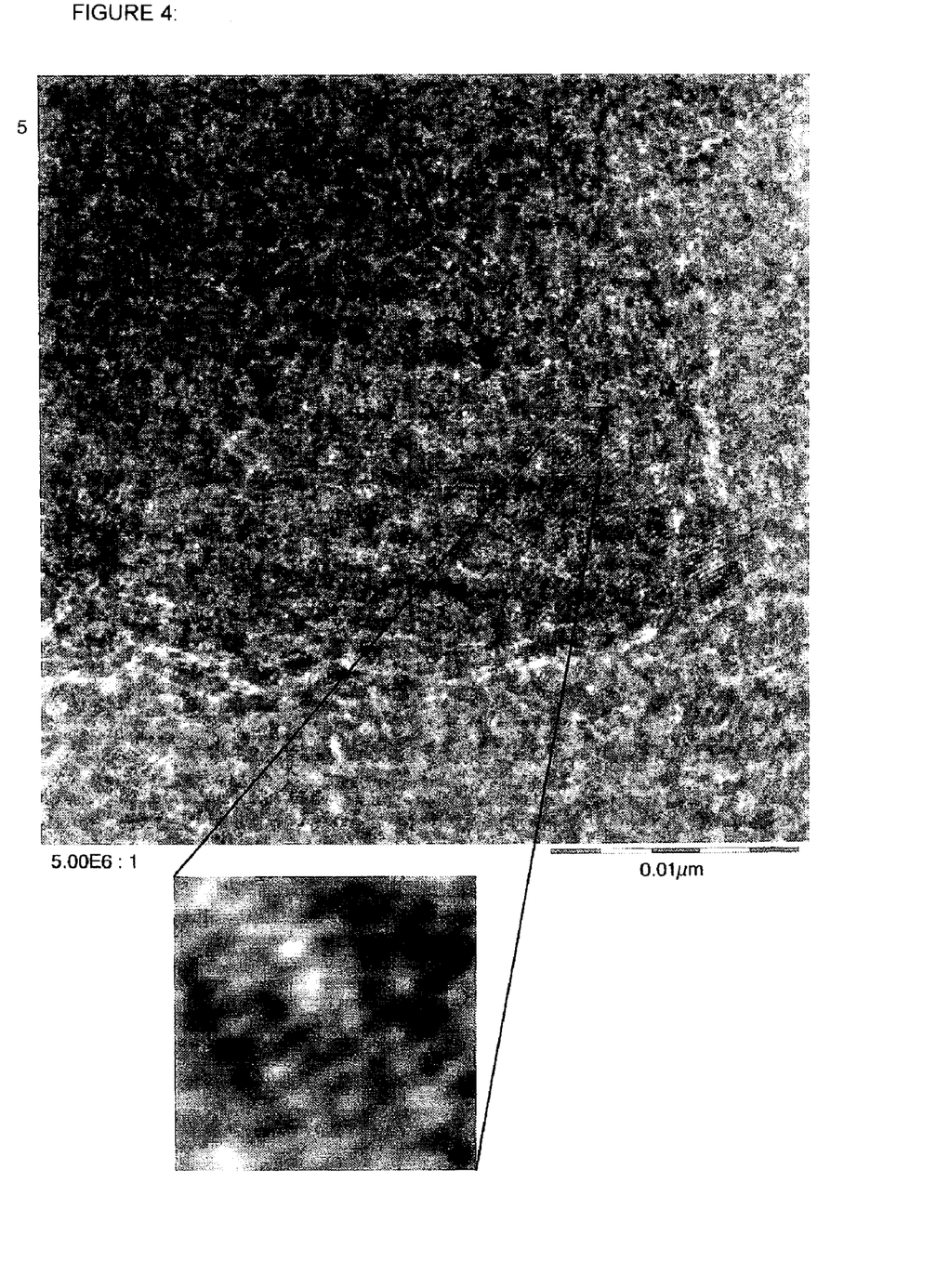
FIG. 4 shows a transmission electron micrograph of the compound of Example 2.

Transmission electron micrographs (TEM) are shown in FIG. 3 and FIG. 4. These clearly show the presence of crystalline substructures.

The transmission electron micrograph is recorded by admixing the sample with a little ethanol and rubbing it between 2 glass microscope slides. This is then spread out thinly and dabbed off with a specimen support grid to which a Formvar/carbon film has been applied. The micrographs were recorded using a 200 kV FEG TEM from FEI. Instrument designation: Tecnai $G^2$.

Example 3

Preparation/Characterization of an Al—BTC MOF 15.6 g of 1,3,5-benzenetricarboxylic acid and 45.8 g of $Al(NO_3)_3*9H_2O$ are suspended in 520.5 g of DMF in a glass flask and stirred under reflux at 130° C. for 4 days. After cooling, the solid is filtered off, washed with 2×100 ml of DMF and 4×100 ml of methanol and dried at 200° C. in a vacuum drying oven for 16 hours. The sample is subsequently after-treated at 330° C. in a muffle furnace (100 l/h of air) for 3 days (heating at about 75° C./h). 17.7 g of an Al—BTC MOF having a surface area of 1696 $m^2/g$ (determined using $N_2$ by the Langmuir method) are obtained. The diffraction pattern (XRD) shows no significant differences from that in example 2.

Example 4

Figure 5:
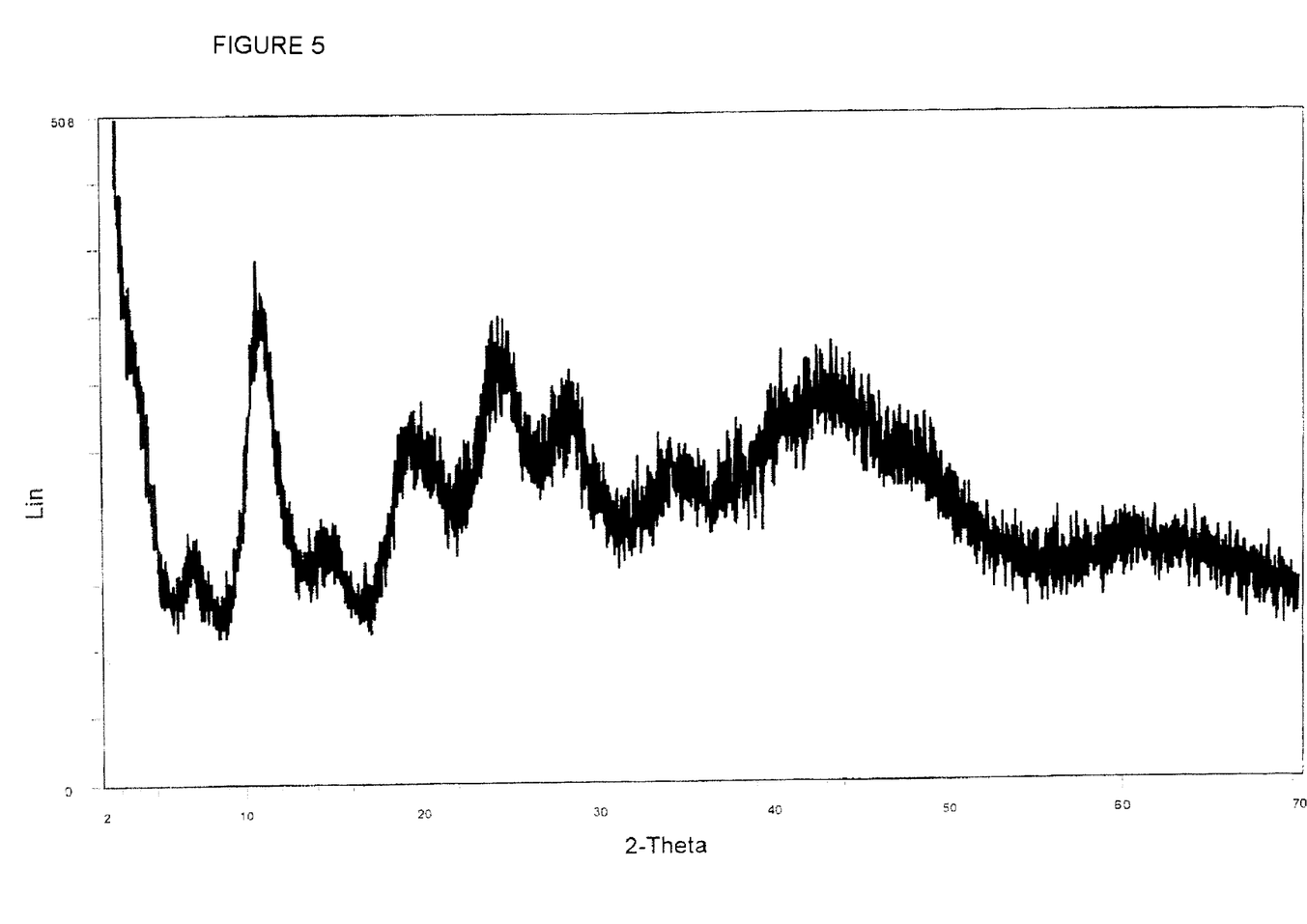
FIG. 5 shows the X-ray diffraction pattern (XRD) of the compound of Example 4.

Preparation/Characterization of an Al—BTC MOF 7.8 g of 1,3,5-benzenetricarboxylic acid and 14.7 g of $AlCl_3*6H_2O$ are suspended in 520.5 g of DMF in a glass flask and stirred under reflux at 130° C. for 4 days. After cooling, the solid is filtered off, washed with 2×100 ml of DMF and 4×100 ml of methanol and dried at 200° C. in a vacuum drying oven for 16 hours. The sample is subsequently after-treated at 330° C. in a muffle furnace (100 l/h of air) for 3 days (heating at about 75° C./h). 10.9 g of an Al—BTC MOF having a surface area of 1451 $m^2/g$ (determined using $N_2$ by the Langmuir method) are obtained. The diffraction pattern (XRD) is shown in FIG. 5.

Example 5

Figure 6:
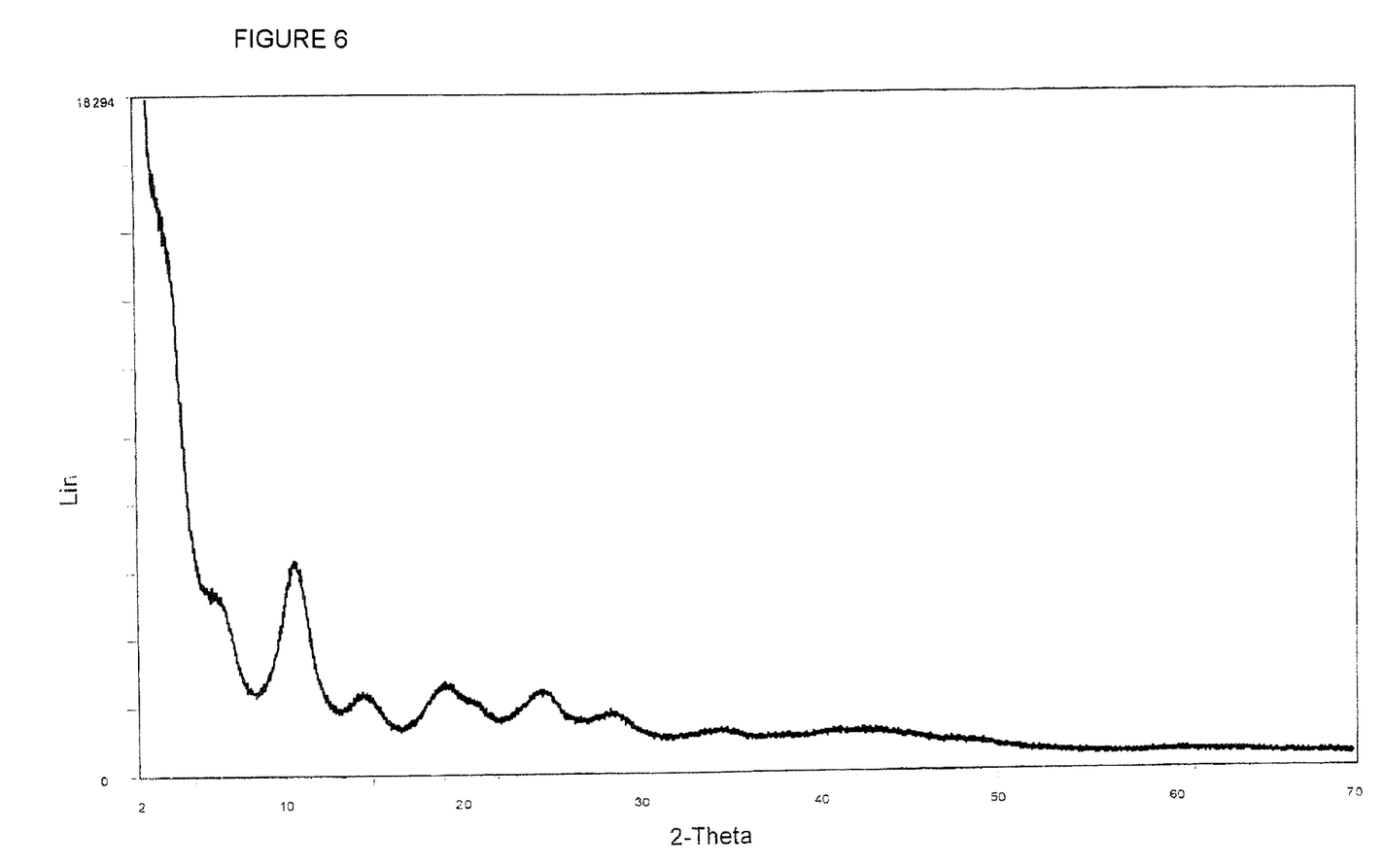
FIG. 6 shows the X-ray diffraction pattern (XRD) of the compound of Example 5.

Preparation/Characterization of an Al—BTC MOF 23.1 g of 1,3,5-benzenetricarboxylic acid and 29.4 g of $AlCl_3*6H_2O$ are suspended in 520.5 g of DMF in a glass flask and stirred under reflux at 130° C. for 4 days. After cooling, the solid is filtered off, washed with 2×100 ml of DMF and 4×100 ml of methanol and dried at 200° C. in a vacuum drying oven for 16 hours. The sample is subsequently after-treated at 330° C. in a muffle furnace (100 l/h of air) for 3 days (heating at about 75° C./h). 12.3 g of an Al—BTC MOF having a surface area of 2033 m²/g (determined using N₂ by the Langmuir method) are obtained. The diffraction pattern (XRD) is shown in FIG. 6.

Example 6

Figure 7:
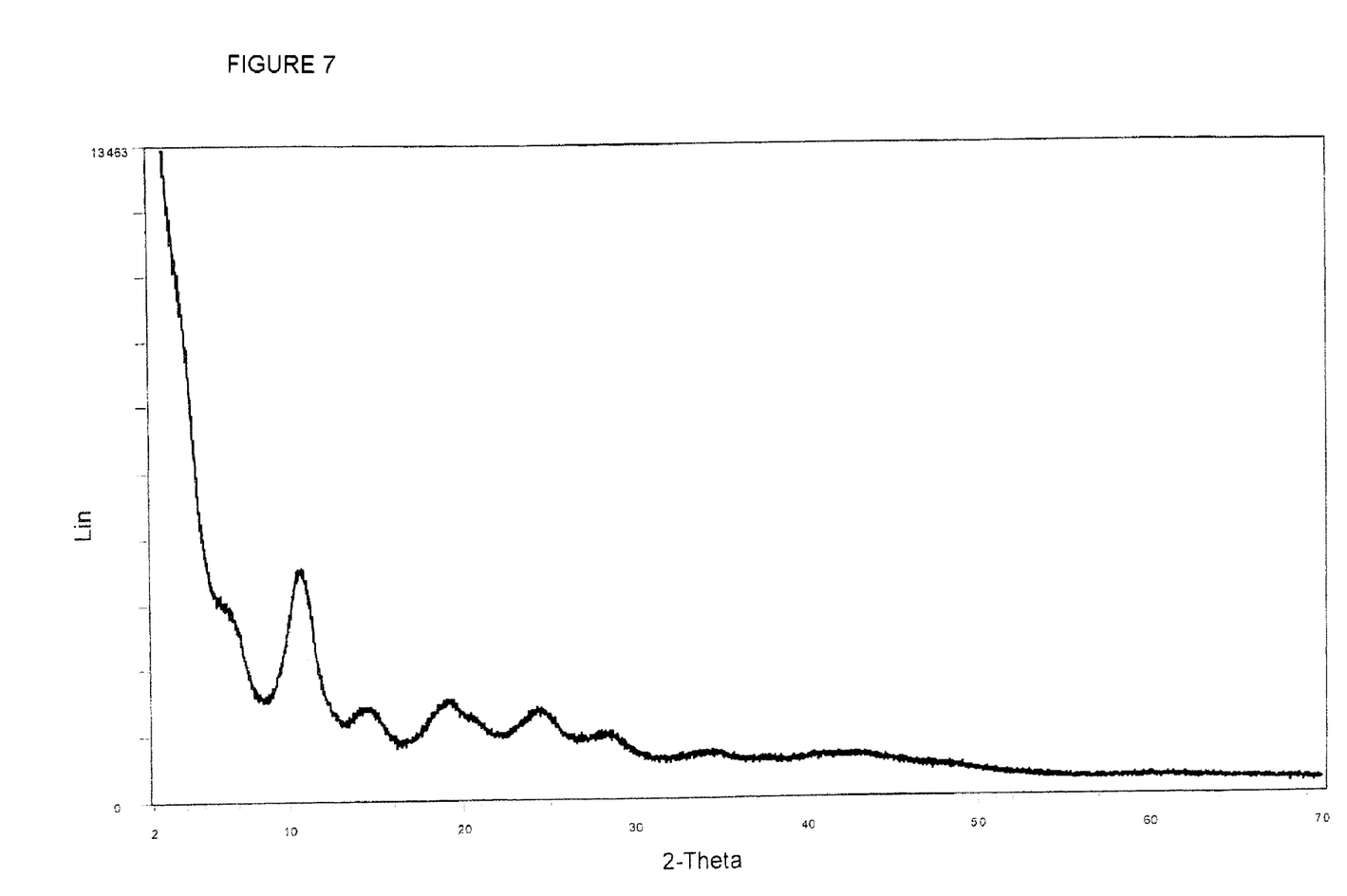
FIG. 7 shows the X-ray diffraction pattern (XRD) of the compound of Example 6.

Preparation/Characterization of an Al—BTC MOF 15.6 g of 1,3,5-benzenetricarboxylic acid and 29.4 g of AlCl₃*6H₂O are suspended in 520.5 g of DMF in a glass flask and stirred under reflux at 130° C. for 4 days. After cooling, the solid is filtered off, washed with 2×100 ml of DMF and 4×100 ml of methanol and dried at 200° C. in a vacuum drying oven for 16 hours. The sample is subsequently after-treated at 330° C. in a muffle furnace (100 l/h of air) for 3 days (heating at about 75° C./h). 20.1 g of an Al—BTC MOF having a surface area of 1898 m²/g (determined using N₂ by the Langmuir method) are obtained. The diffraction pattern (XRD) is shown in FIG. 7.

Example 7

Storage of Hydrogen in an Al—BTC MOF 314 mg of the framework from example 1 are firstly evacuated at 200° C. Hydrogen is subsequently absorbed with the aid of a Quantachrome Autosorb 1 instrument at 77 K. A hydrogen uptake of about 100 ml/g was obtained at $p/p_0=6.5*10^{-3}$.

The invention claimed is:

1. A porous metal-organic framework comprising at least one at least bidentate organic compound coordinated to at least one metal ion, wherein the at least one metal ion is $Al^{III}$ and the at least one at least bidentate organic compound is a six-membered aromatic hydrocarbon ring A in which one or more ring carbons may be replaced by nitrogen and which has three substituents X and optionally one or more substituents selected from the group consisting of R, NRR', OR, SR, F, Cl and Br, where R, R' are each, independently of one another, hydrogen, methyl which may optionally be substituted by one or more fluorine atoms or ethyl which may optionally be substituted by one or more fluorine atoms and each X is, independently of the others, C(=O)O⁻, C(=S)O⁻, C(=O)S⁻, C(=S)S⁻ or a protonated form thereof, characterized in that the metal-organic framework in powder has a specific surface area determined by the Langmuir method of at least 800 m²/g.

2. The framework according to claim 1, wherein A is benzene, pyridine, pyridazine, pyrimidine, pyrazine or triazine.

3. The framework according to claim 1, wherein the at least one at least bidentate organic compound is 1,3,5-, 1,2,3-, 1,2,4-benzenetricarboxylate or a protonated form thereof.

4. The framework according to claim 1 which has a mole fraction of the at least one at least bidentate organic compound of at least 50% of the total amount of the organic compounds.

5. The framework according to claim 1, wherein at least 50% of the pore volume is formed by pores having a pore diameter of from 2 to 10 nm and the most frequently occurring pore diameter is preferably in the range from 3 to 9 nm.

6. The framework according to claim 1 whose pore volume is at least 0.8 mg/l.

7. The framework according to claim 1 which in powder form has a specific surface area determined by the Langmuir method of at least 1000 m²/g.

8. A process for preparing a framework according to claim 1, which comprises
reacting of at least one metal compound with at least one at least bidentate organic compound which can coordinate to the metal ion, wherein the metal is $Al^{III}$ and the at least one at least bidentate organic compound is a six-membered aromatic hydrocarbon ring A in which one or more ring carbons may be replaced by nitrogen and which has three substituents X and optionally one or more substituents selected from the group consisting of R, NRR', OR, SR, F, Cl and Br, where R, R' are each, independently of one another, hydrogen, methyl which may optionally be substituted by one or more fluorine atoms or ethyl which may optionally be substituted by one or more fluorine atoms and each X is, independently of the others, C(=O)O⁻, C(=S)O⁻, C(=O)S⁻, C(=S)S⁻ or a protonated form thereof.

9. The process according to claim 8, wherein the framework formed is after-treated with an organic solvent and/or calcined after the reaction.

10. The process according to claim 8, wherein $Al^{III}$ is made available for the reaction by means of anodic oxidation.

11. A method of using the framework according to claim 1 comprising uptaking at least one substance and storing, separating, controlledly releasing or chemically reacting the at least one substrate.

12. The method according to claim 11 for the storage of hydrogen.

13. The method according to claim 11 for diffusion-limited reaction with large-volume reactants.

14. A support material comprising the framework according to claim 1.

* * * * *